(12) United States Patent
Nelissen

(10) Patent No.: US 8,517,029 B2
(45) Date of Patent: Aug. 27, 2013

(54) DEVICE FOR TREATING NIGHT TIME BREATHING PROBLEMS

(76) Inventor: Jozef Frans Nelissen, Nijlen (BE)

(*) Notice: Subject to any disclaimer, the term of this patent is extended or adjusted under 35 U.S.C. 154(b) by 88 days.

(21) Appl. No.: 13/002,499

(22) PCT Filed: Jul. 6, 2009

(86) PCT No.: PCT/BE2009/000037
§ 371 (c)(1),
(2), (4) Date: Mar. 15, 2011

(87) PCT Pub. No.: WO2010/003198
PCT Pub. Date: Jan. 14, 2010

(65) Prior Publication Data
US 2011/0168187 A1    Jul. 14, 2011

(30) Foreign Application Priority Data
Jul. 7, 2008  (BE) .................................. 2008/0374

(51) Int. Cl.
*A61F 5/56*    (2006.01)
(52) U.S. Cl.
USPC .......................................... 128/848; 128/859
(58) Field of Classification Search
USPC ....................... 128/848, 859, 861, 862; 433/6
See application file for complete search history.

(56) References Cited

U.S. PATENT DOCUMENTS

| 5,868,138 A | 2/1999 | Halstrom |
| 6,604,527 B1 * | 8/2003 | Palmisano ..................... 128/848 |
| 7,007,697 B1 | 3/2006 | Della Grotta |
| 2007/0283967 A1 | 12/2007 | Bailey |

FOREIGN PATENT DOCUMENTS

| EP | 1516604 A1 | 3/2005 |
| EP | 1972311 A1 | 9/2008 |
| WO | 2005013867 | 2/2005 |
| WO | 2007113465 | 10/2007 |
| WO | WO 2008060122 A1 * | 5/2008 |

* cited by examiner

*Primary Examiner* — Patricia Bianco
*Assistant Examiner* — Keri J Nelson
(74) *Attorney, Agent, or Firm* — Bozicevic, Field & Francis LLP; Bret E. Field

(57) ABSTRACT

Device (1) for treating breathing problems, comprising a lower part (2) mountable on the lower jaw and an upper part (3) mountable on the upper jaw; and left and right coupling means (4) for coupling the lower part to the upper part close to the back teeth; wherein each of the left and right coupling means comprises an upper coupling element (6) connected to the upper part and a lower coupling element (5) connected to the lower part; which left and right coupling means are adapted to move the lower jaw forward in relation to the upper jaw, wherein the upper coupling element is provided with a stop (13) for co-action with a contact surface (12) of the lower coupling element.

18 Claims, 6 Drawing Sheets

DEVICE FOR TREATING NIGHT TIME BREATHING PROBLEMS

The present invention relates to a device for treating breathing problems, comprising
- a lower part mountable on the lower jaw and an upper part mountable on the upper jaw, which lower and upper parts are situated at least in the vicinity of the back teeth; and
- left and right coupling means for coupling the lower part to the upper part close to the back teeth; wherein each of the left and right coupling means comprises an upper coupling element connected to the upper part and a lower coupling element connected to the lower part; which left and right coupling means are adapted to move the lower jaw forward in relation to the upper jaw.

Night-time breathing problems, which can for instance result in snoring, sleep apnea syndrome or other sleep disorders are a generally known problem. When a person sleeps, the rear part of the tongue may tend to slide backwards, whereby the pharyngeal airway is wholly or partially closed off. It is known to solve such breathing problems with a device which can be placed in the mouth and with which the lower jaw is placed further forward in relation to the upper jaw. The neck muscles are hereby forced into a tensioned position, whereby the tongue moves forward and the airway is left clear.

Said devices placeable in the mouth are generally known and can be found in a number of different embodiments, including embodiments as described in the preamble which have been known since the 1990s. The known embodiments have the drawback that they allow too much freedom of movement during opening/closing of the mouth.

US 2007/0283967 and WO 2007/113465 both describe oral appliances in which coupling means are provided between the lower and upper tooth arches. Such appliances prevent the tongue being in a position of rest and offer only limited possibilities for control.

The invention has for its object to provide a device according to the preamble of claim 1, which is user-friendly and agreeable to wear, and allows a precise adjustment with a limited freedom of movement of the lower jaw in relation to the upper jaw.

The invention is distinguished for this purpose in that the upper coupling element is provided with a stop for co-action with a contact surface of the lower coupling element, such that when lower and upper jaw are moved towards each other a further closing of the mouth is prevented when the contact surface comes up against the stop. The left and right, upper and lower coupling elements are further connected to respectively the upper and lower part such that they are situated in the oral vestibule (vestibulum oris) in the position of the device placed in the mouth, i.e. the coupling elements are situated between the teeth and respectively the left and right cheek.

In this way the freedom of movement of the lower jaw in relation to the upper jaw is also limited in vertical direction, i.e. in a direction substantially perpendicular to the plane of the lower jaw or upper jaw.

According to an advantageous embodiment, at least one coupling element of the upper and the lower coupling elements is provided with vertical adjusting means for adjusting the vertical position of the stop/the contact surface in relation to the lower jaw in order to obtain an adjustable minimum distance between lower jaw and upper jaw.

According to an aspect of the invention, the at least one coupling element comprises a contact portion and a base portion connected respectively to the upper or lower part, wherein vertical adjusting means are provided between the contact portion and the base portion for the purpose of adjusting the vertical position of the contact portion in relation to the base portion. By increasing the distance between the contact portion and the base portion the contact portion (on which the contact surface or the stop is situated) thus comes to lie further from respectively the upper part or the lower part, and the freedom of movement is thus further limited.

According to a possible embodiment, the adjusting means comprise a substantially vertical adjusting screw with double screw thread for the up/downward adjustment of the contact portion in relation to the base portion, which adjusting screw co-acts at one outer end with a first threaded bore in the contact portion and co-acts at its other outer end with a second threaded bore in the base portion, wherein a rotation of the adjusting screw changes the distance between the first and second threaded bore. According to a further developed embodiment, the adjusting screw is provided substantially in the centre with an encircling flange with radially directed openings into which a rod fits for the purpose of rotating the adjusting screw by rotating the rod. In this way the vertical distance can be adjusted in convenient manner. Telescopically acting tubes between base portion and contact portion can further be provided on either side of the vertical adjusting screw so as to thus improve the stability of the device.

According to another aspect of the invention, at least one coupling element of the upper and the lower coupling element comprises a fixed part which is connected to respectively the lower part or upper part, and a part which is displaceable relative to this fixed part substantially parallel to respectively the lower part or upper part. "Parallel to respectively the lower part or upper part" should be understood to mean substantially parallel to the plane of respectively the lower teeth or the upper teeth when the device is placed in the mouth. In this way the moving forward of the lower jaw in relation to the upper jaw can likewise be adjusted.

According to a possible embodiment, the displaceable part comprises the contact portion such that both a horizontal and vertical displacement are possible. Horizontal should here be understood to mean substantially parallel to the plane of respectively the lower teeth or the upper teeth when the device is placed in the mouth, depending on whether the displaceable part is situated in respectively the upper or lower coupling element. Vertical should then be understood to mean substantially perpendicular to respectively the plane of the lower jaw or of the upper jaw.

According to yet another aspect of the invention, each upper coupling element is provided with a substantially vertical portion with a concave or convex surface directed toward the front teeth, and each lower coupling element is provided with a substantially complementarily shaped surface, this such that the upper coupling element can engage in the lower coupling element and that rearward movement of the lower jaw is avoided. In this way the vertical movement of upper coupling element in relation to lower coupling element is further guided and limited, while a lateral movement of upper jaw in relation to lower jaw is a possibility, as will be further elucidated.

According to a preferred embodiment of the invention, the upper and lower coupling elements are designed such that a limited lateral or sideways movement of the lower part arranged on the lower jaw in relation to the upper part arranged on the upper jaw, i.e. a movement in the plane of the teeth and substantially perpendicularly of the back teeth, is possible. A limited lateral freedom of movement further increases the wearing comfort without having serious consequences for the accuracy of adjustment. According to a possible embodiment, the lower coupling element lies in lateral direction at a distance from the upper part in the position of the device placed in the mouth.

Other features and advantages will become apparent from the description of a number of non-limitative exemplary embodiments with reference to the accompanying drawings, in which:

FIG. 1 shows a perspective view of a preferred embodiment of a device according to the invention;

FIGS. 2(A)-(F) show schematic side views of different variants of the embodiment of FIG. 1;

In the drawings of the different embodiments equivalent components are designated with the same reference numerals, wherein a hundred is added at a time for each variant.

Figure 1:
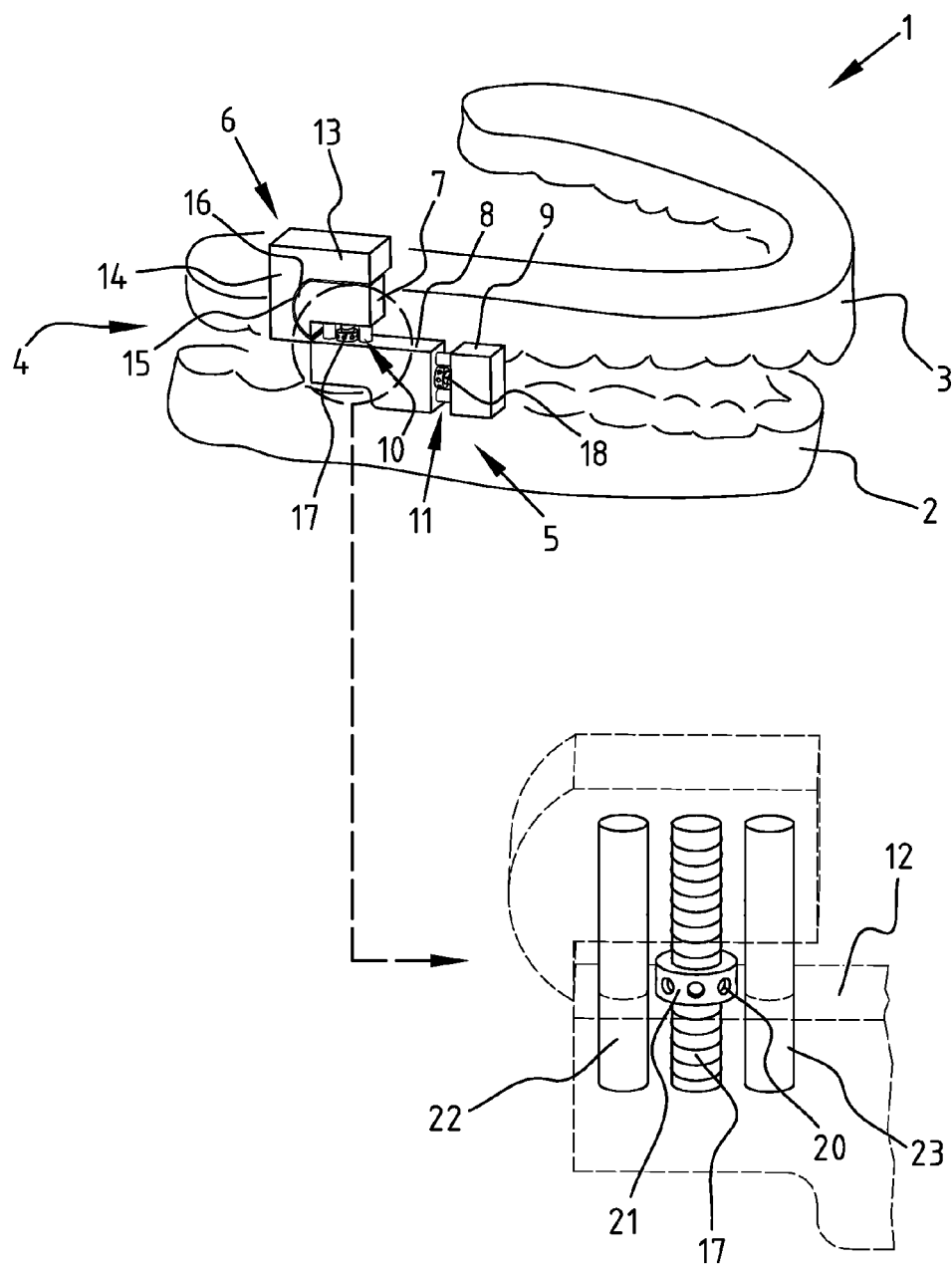
Figure 3A:
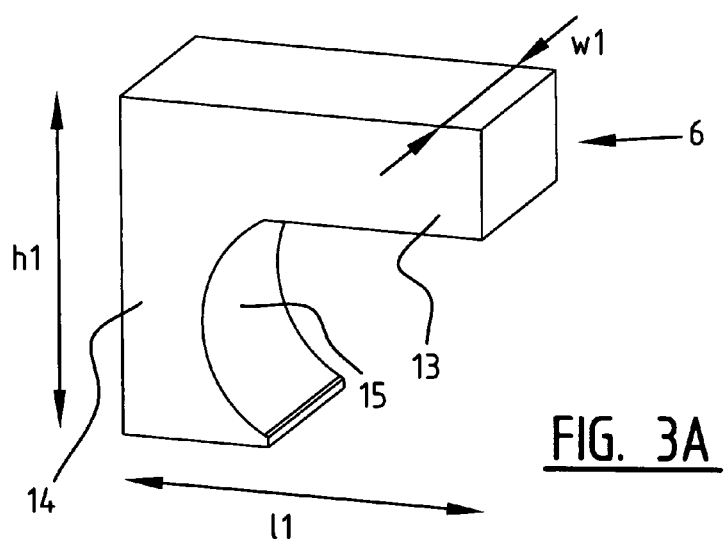
FIG. 3 (A) shows a perspective detail view of an upper coupling element of the embodiment of FIG. 1.
FIG. 3(B) shows a perspective detail view of a lower coupling element of the embodiment of FIG. 1.
Figure 4:
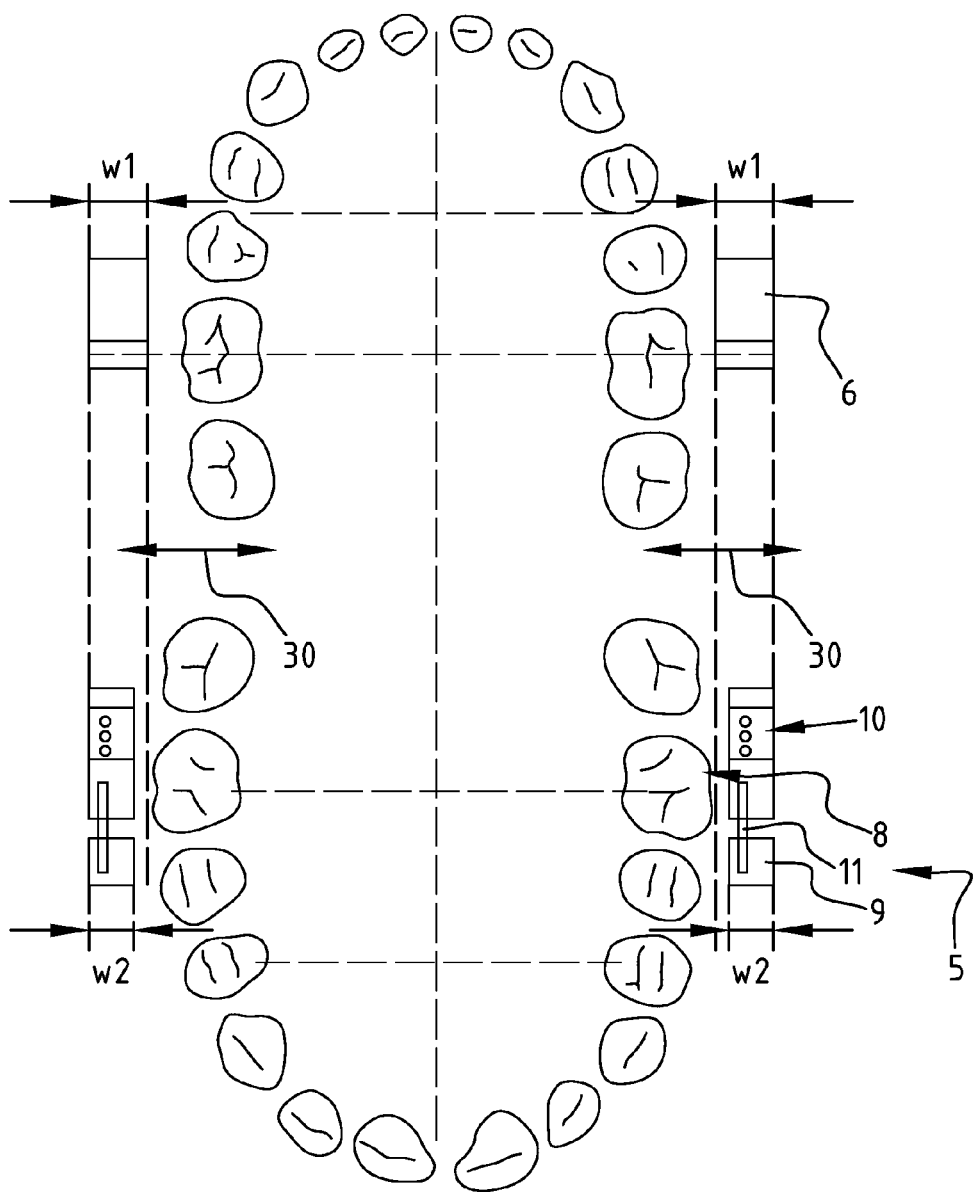
FIG. 4 shows a top view of the upper and lower coupling element placed on an upper and lower jaw.

FIG. 1 and FIGS. 3(A) & (B) and FIG. 4 illustrate a preferred embodiment of an oral apparatus 1 for treating breathing problems. This apparatus 1 comprises a lower part mountable on the lower jaw in the form of a shaped part 2 and an upper part mountable on the upper jaw in the form of a shaped part 3. The skilled person will understand that the lower and upper part may also be embodied differently and the term part is understood to mean for instance a brace with a palate plate as well as a flexible bite-block. The only requirement is that the lower and upper parts are situated at least in the vicinity of the back teeth such that coupling elements can there be mounted on the lower/upper part 2, 3.

The apparatus further comprises left and right coupling means 4 (for the sake of simplicity only the left coupling means are shown in FIG. 1) for coupling lower part 2 to upper part 3 close to the back teeth. Each of the left and right coupling means 4 comprises an upper coupling element 6 connected to upper part 3 and a lower coupling element 5 connected to lower part 2. In the position of lower and upper part placed in the mouth these coupling means 4 are situated on the vestibular side of the tooth arch, i.e. between the cheek and the tooth arches. As will become further apparent, the left and right coupling means 4 are adapted to move the lower jaw forward in relation to the upper jaw, while the up/downward movement of the lower jaw in relation to upper jaw is also controlled.

In the embodiment of FIG. 1 lower coupling element 5 consists of three parts: a fixed part 9, a central part 8, and an upper part 7. Fixed part 9 is attached to lower part 2 and connected via horizontal adjusting means 11 to central part 8. Central part 8 is connected via vertical adjusting means 10 to upper part 7. Part 7 functions here as a contact portion with a contact surface 12 for the purpose of making contact with a stop 13 of upper coupling element 6 when the mouth is closed. Parts 8 and 9 can be seen as a base portion. Contact portion 7 can be moved upward/downward in relation to base portion 8, 9 using adjusting means 10.

Central part 8 is further horizontally displaceable in relation to fixed part 9 via adjusting means 11, wherein horizontally is understood to mean substantially parallel to lower part 2. Parts 7 and 8 thus form a block which is horizontally displaceable in relation to fixed part 9. Parts 7, 8 and 9 with associated adjusting means thus allow adjustment of both the vertical and the horizontal position of contact surface 12 in order to obtain an adjustable minimum vertical and horizontal distance between lower jaw and upper jaw.

Upper coupling element 6 is provided with a substantially vertical portion 14 with a concave surface 15 directed toward the front teeth, and contact portion 7 of lower coupling element 5 is provided with a substantially complementarily shaped surface 16. In this way the upper coupling element can engage in the lower coupling element and the vertical movement of lower jaw in relation to upper jaw is further guided and limited.

According to the illustrated embodiment, the vertical and horizontal adjusting means 10, 11 consist in each case of a central adjusting screw 17, 18 with double screw thread for respectively up/downward and front/backward adjustment of contact portion 7 relative to fixed part 9. Arranged on either side of each central adjusting screw 17, 18 are telescopically acting tubes 22, 23 and 24, 25 parallel thereto (see in particular FIG. 3(B)). The central vertical adjusting screw 17 co-acts at one outer end with a first threaded bore in contact portion 7 and at its other outer end with a second threaded bore in central part 8, wherein a rotation of the adjusting screw changes the distance between the first and second threaded bore. The central horizontal adjusting screw 18 co-acts on one side with a threaded bore in central part 8 and on the other with a threaded bore in fixed part 9. Each adjusting screw 17, 18 is preferably provided substantially in the centre with an encircling flange 21 with radially directed openings 20 into which a rod fits for the purpose of rotating the adjusting screw by rotating the rod.

Figure 3B:
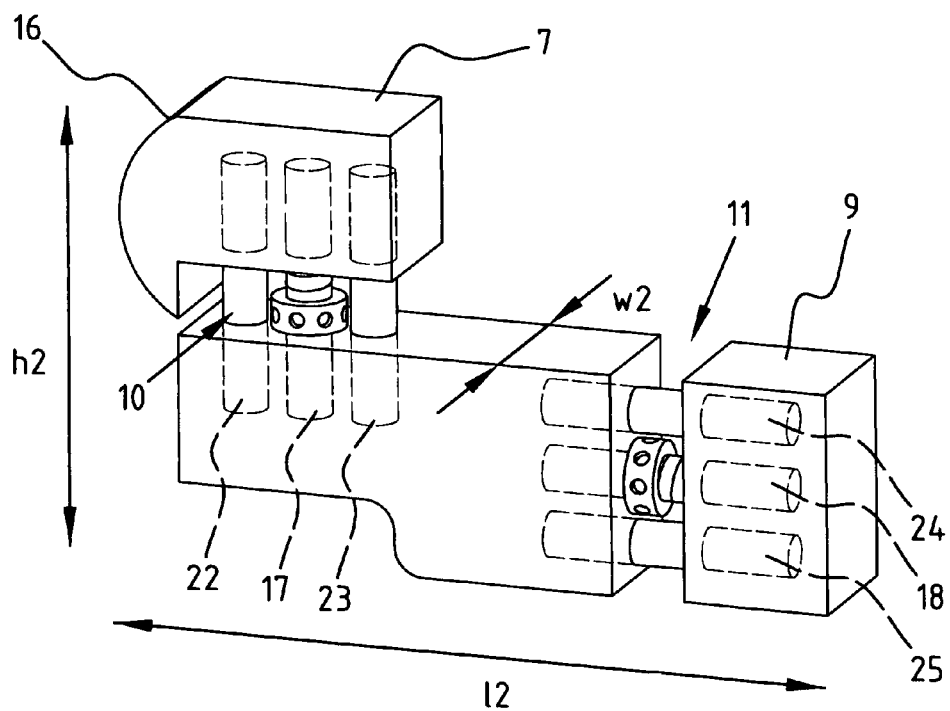

FIG. 3(A) shows upper coupling element 6 in detail. The dimensions of this element 6 can for instance be as follows:
width w1 between 5 and 10 mm, preferably about 8 mm;
height h1 between 10 and 20 mm, preferably about 15 mm;
length l1 between 10 and 20 mm, preferably about 15 mm.
FIG. 3(B) shows lower coupling element 5 in detail. The dimensions of this element 5 can for instance be as follows:
width w2 smaller than width w1, for instance between 4 and 9 mm, preferably about 2 mm smaller than w1 and so more preferably about 6 mm;
height h2 between 15 and 25 mm, preferably about 18 mm;
length l2 between 20 and 40 mm, preferably about 32 mm.

According to an advantageous embodiment, each upper coupling element 6 can move laterally or sideways in limited manner (see arrow 30 in FIG. 4) in relation to the lower coupling element in a position of the oral apparatus placed in the mouth. In an advantageous embodiment shown in FIG. 4 the width w2 of upper coupling element 6 is for this purpose smaller than the width w1 of lower coupling element 5, and the lower coupling element is placed further outward (here over a distance w1-w2, although the skilled person will appreciate that this distance may also be to some extent smaller or greater). In this way lower coupling element 5 will be situated at a distance in lateral direction from the upper part when the device is placed in the mouth, and will thus allow a lateral movement of upper part in relation to lower part.

A number of variants will now be described with reference to the schematic side views shown in FIGS. 2(A)-(E), in which for the sake of clarity the lower and upper parts are not shown.

Figure 2A:
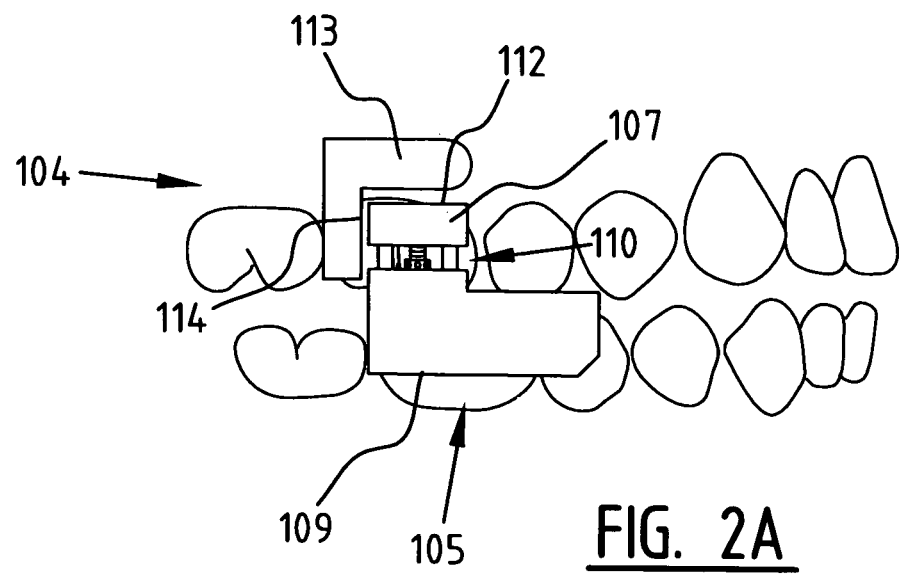

In the variant of FIG. 2(A) the coupling means 104 do not comprise horizontal adjusting means and lower coupling element 105 consists of two parts: a base portion 109 and a contact portion 107. Contact portion 107 has a contact surface 112, the height of which is adjustable using vertical adjusting means 110. The contact surface 112 is for the purpose of making contact with a stop 113 of upper coupling element when the mouth is closed. Upper coupling element is further provided with a substantially vertical portion 114.

Figure 2B:
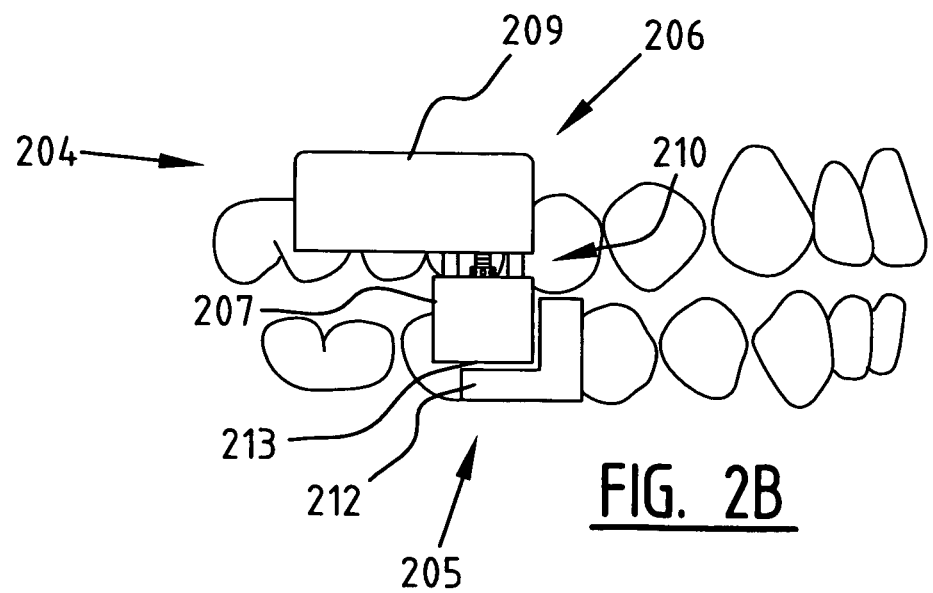

FIG. 2(B) shows an equivalent variant of coupling means 204 wherein base portion 209 and the vertically adjustable contact portion 207 are provided in upper coupling element 206 and stop 213 is situated on the bottom of contact portion 207, while contact surface 212 is provided on lower coupling element 205. Vertical adjusting means 210 connect the contact portion 207 with the base portion 209.

Figure 2C:
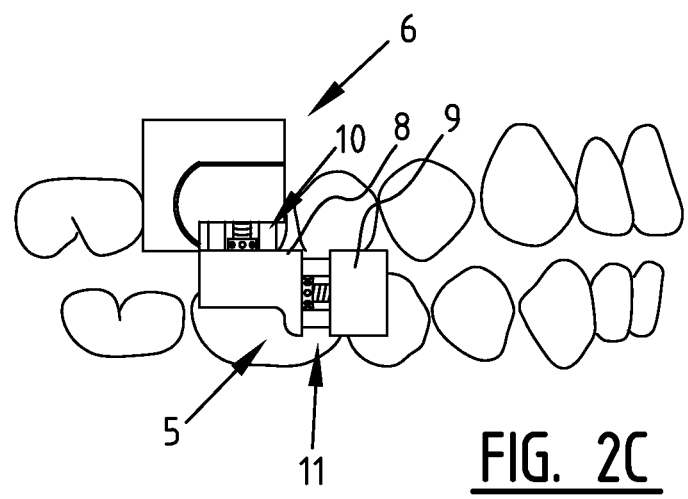
Figure 2D:
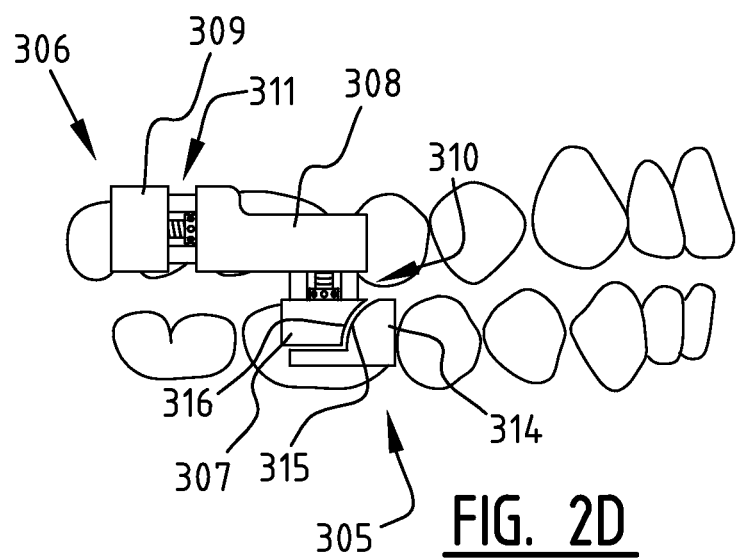

The variant of FIG. 2(C) largely corresponds with the embodiment of FIG. 1, so that reference can be made to the description above of FIG. 1. FIG. 2(D) shows a reverse variant in which parts 307, 308 and 309 with associated vertical and horizontal adjusting means 310, 311 are received in upper coupling element 306. Lower coupling element 305 is provided here with a vertical portion 314 with a convex surface 315 and contact portion 307 is formed with a complementarily formed surface 316.

Figure 2E:
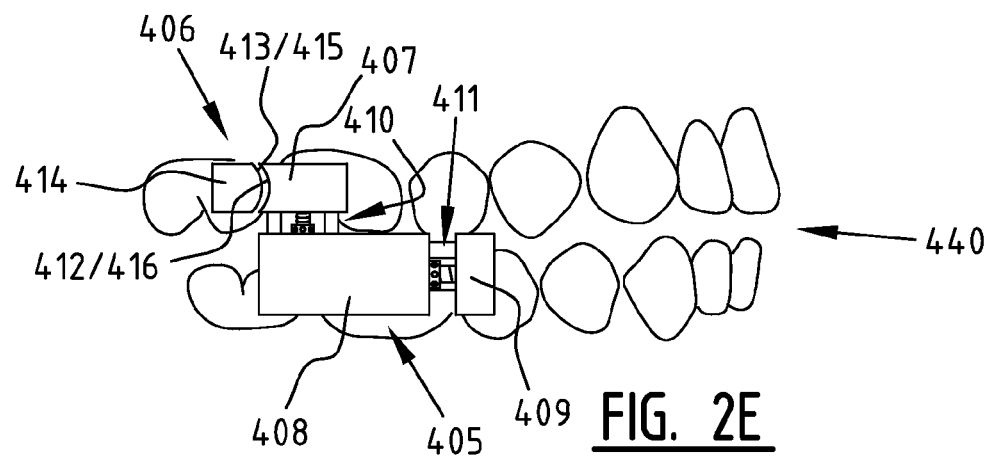
Figure 2F:
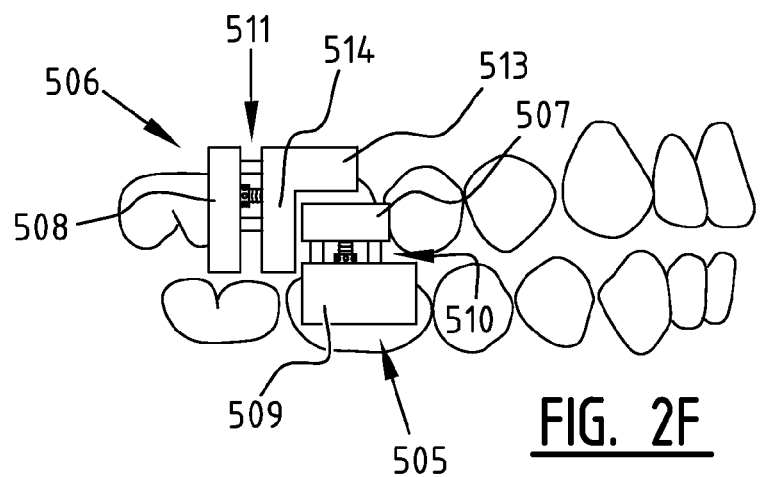

FIG. 2(E) shows a variant in which the upper coupling element 406 is provided with a vertical portion 414 with a convex surface 415 directed toward the front teeth 440. This convex surface thus forms on one side a stop 413 for contact portion 407 of lower coupling element 405, which contact portion prevents the closing movement and on the other a guide surface for guiding and limiting the vertical movement of part 407 which is provided with a complementary surface 412/416. Fixed part 409 is connected via horizontal adjusting means 411 to central part 408. Central part 408 is connected via vertical adjusting means 410 to upper part 407. Finally, FIG. 2(F) shows a variant in which the horizontal adjusting means 511 are provided in upper coupling element 506 between a fixed part 508 mounted on the upper part and a stop part with a vertical portion 514 and with a stop 513. The vertical adjusting means 510 are provided in lower coupling element 505 between a contact portion 507 and a fixed part 509.

The skilled person will appreciate that the figures are not limitative and that measures of one variant may be added to another variant without departing from the scope of the invention. The design of element 513, 514 on the one hand and element 507 on the other of the embodiment of FIG. 2F, can for instance thus be modified and be for instance analogous to the design of element 13, 14 on the one hand and element 7 on the other of the embodiment of FIG. 1.

The invention is not limited to the exemplary embodiments illustrated above and the skilled person will understand that many modifications can be envisaged without departing from the scope of the invention, this scope being defined solely by the following claims.

The invention claimed is:

1. A device for treating breathing problems, the device comprising
    a lower part mountable on the lower jaw and an upper part mountable on the upper jaw, which lower and upper parts are situated at least in the vicinity of the back teeth; and
    left and right coupling means for coupling the lower part to the upper part close to the back teeth;
    wherein each of the left and right coupling means comprises an upper coupling element connected to the upper part and a lower coupling element connected to the lower part;
    which left and right coupling means are adapted to move the lower jaw forward in relation to the upper jaw;
    wherein the upper and lower coupling elements are connected to respectively the upper and lower part such that these upper and lower coupling elements are situated in the oral vestibule in the position of the device placed in the mouth, and
    wherein the upper coupling element is provided with a stop having a lower surface for co-action with an upper contact surface of the lower coupling element, such that when the lower part is coupled to the upper part and the lower jaw and upper jaw are moved toward each other, a further closing of the mouth is prevented when the contact surface comes up against the stop.

2. The device according to claim 1, wherein at least one coupling element of the upper and the lower coupling element is provided with vertical adjusting means for adjusting the vertical position of the lower surface of the stop in relation to the lower jaw in order to obtain an adjustable minimum distance between lower jaw and upper jaw.

3. The device according to claim 2, wherein the at least one coupling element of the upper and the lower coupling element comprises a contact portion and a base portion connected to the upper or lower part, and that the vertical adjusting means are provided between the contact portion and the base portion for the purpose of adjusting the vertical position of the contact portion in relation to the base portion.

4. The device according to claim 3, wherein the adjusting means comprise a substantially vertical adjusting screw with double screw thread for the upward and downward adjustment of the contact portion in relation to the base portion, which adjusting screw co-acts at one outer end with a first threaded bore in the contact portion and co-acts at its other outer end with a second threaded bore in the base portion, wherein a rotation of the adjusting screw changes the distance between the first and second threaded bore.

5. The device according to claim 4, wherein the adjusting screw is provided substantially in the centre with an encircling flange with radially directed openings into which a rod fits for the purpose of rotating the adjusting screw by rotating the rod.

6. The device according to claim 5, wherein telescopically acting tubes between base portion and contact portion are provided on either side of the vertical adjusting screw.

7. The device according to claim 4, wherein telescopically acting tubes between base portion and contact portion are provided on either side of the vertical adjusting screw.

8. The device according to claim 3, wherein at least one coupling element of the upper and the lower coupling element comprises a fixed part which is connected to respectively the lower part or upper part, and a part which is displaceable relative to this fixed part parallel to respectively the lower part or upper part.

9. The device according to claim 1, wherein at least one coupling element of the upper and the lower coupling element comprises a fixed part which is connected to respectively the lower part or upper part, and a part which is displaceable relative to this fixed part parallel to respectively the lower part or upper part.

10. The device according to claim 9, wherein the displaceable part comprises the contact portion.

11. The device according to claim 8, wherein the displaceable part comprises the contact portion.

12. The device according to claim 1, wherein each upper coupling element is provided with a portion with a concave or convex surface directed toward the front teeth, and that each lower coupling element is provided with a substantially complementarily shaped surface, this such that the upper coupling element is engageable in the lower coupling element and that rearward movement of the lower jaw is avoided.

13. The device according to claim 1, wherein a limited lateral or sideways movement of the lower part arranged on the lower jaw in relation to the upper part arranged on the upper jaw is permitted with the device positioned in the mouth and with the lower surface of the stop in contact with the upper contact surface of the lower coupling element;

wherein the lateral or sideways movement is in the plane of the teeth and substantially perpendicularly of the back teeth.

14. The device according to claim 13, wherein each lower coupling element has in lateral direction a width differing from the associated upper coupling element such that a lateral clearance is obtained which allows a lateral movement of the lower jaw in relation to the upper jaw.

15. The device according to claim 1, wherein in the case of both the left and the right coupling means one coupling element of the upper and lower coupling element is situated in lateral direction at a distance from the associated upper or lower part in the position of the device placed in the mouth.

16. The device according to claim 15, wherein each lower coupling element has in lateral direction a width differing from the associated upper coupling element such that a lateral clearance is obtained which allows a lateral movement of the lower jaw in relation to the upper jaw.

17. A device for treating breathing problems, the device comprising a lower part mountable on the lower jaw and an upper part mountable on the upper jaw, which lower and upper parts are situated at least in the vicinity of the back teeth; and left and right coupling means for coupling the lower part to the upper part close to the back teeth;

wherein each of the left and right coupling means comprises an upper coupling element connected to the upper part and a lower coupling element connected to the lower part;

which left and right coupling means are adapted to move the lower jaw forward in relation to the upper jaw;

wherein the upper and lower coupling elements are connected to respectively the upper and lower part such that these upper and lower coupling elements are situated in the oral vestibule in the position of the device placed in the mouth, and wherein the upper coupling element is provided with a stop for co-action with a contact surface of the lower coupling element, such that when lower jaw and upper jaw are moved toward each other a further closing of the mouth is prevented when the contact surface comes up against the stop;

wherein at least one coupling element of the upper and the lower coupling element is provided with vertical adjusting means for adjusting the vertical position of the contact surface in relation to the lower jaw in order to obtain an adjustable minimum distance between lower jaw and upper jaw;

wherein the at least one coupling element of the upper and the lower coupling element comprises a contact portion and a base portion connected to the upper or lower part, and that the vertical adjusting means are provided between the contact portion and the base portion for the purpose of adjusting the vertical position of the contact portion in relation to the base portion.

18. A device for treating breathing problems, the device comprising a lower part mountable on the lower jaw and an upper part mountable on the upper jaw, which lower and upper parts are situated at least in the vicinity of the back teeth; and left and right coupling means for coupling the lower part to the upper part close to the back teeth;

wherein each of the left and right coupling means comprises an upper coupling element connected to the upper part and a lower coupling element connected to the lower part;

which left and right coupling means are adapted to move the lower jaw forward in relation to the upper jaw;

wherein the upper and lower coupling elements are connected to respectively the upper and lower part such that these upper and lower coupling elements are situated in the oral vestibule in the position of the device placed in the mouth, and wherein each upper coupling element is provided with a portion with a concave or convex surface directed toward the front teeth, and that each lower coupling element is provided with a substantially complementarily shaped surface, such that the upper coupling element is engageable in the lower coupling element and that rearward movement of the lower jaw is avoided.

* * * * *